United States Patent [19]

Ramella

[11] Patent Number: 4,969,455
[45] Date of Patent: Nov. 13, 1990

[54] INHALATOR FOR AEROSOL CONTAINERS

[75] Inventor: Paolo Ramella, Milan, Italy

[73] Assignee: Somova S.p.A., Milan, Italy

[21] Appl. No.: 358,615

[22] Filed: May 30, 1989

[30] Foreign Application Priority Data

Nov. 29, 1988 [IT] Italy ............................. 22216/88[U]

[51] Int. Cl.$^5$ ............................................. A61M 11/00
[52] U.S. Cl. ............................ 128/200.23; 128/200.14
[58] Field of Search ........................ 128/200.14, 200.23,
128/203.15, 203.21; 222/402.12, 402.2, 538

[56] References Cited

U.S. PATENT DOCUMENTS

| | | | |
|---|---|---|---|
| 3,276,641 | 10/1966 | Lehmann | 222/538 |
| 3,358,890 | 12/1967 | Dalfo | 222/538 |
| 3,429,310 | 2/1969 | Jaffe et al. | 128/200.23 |
| 3,429,483 | 2/1969 | Micallef | 222/402.12 |
| 3,484,023 | 12/1969 | Meshberg | 222/402.12 |
| 3,739,950 | 6/1973 | Gorman | 128/200.23 |
| 3,847,313 | 11/1974 | Micsllef | 222/538 |
| 3,935,973 | 2/1976 | Weyn | 222/402.12 |
| 4,096,974 | 6/1978 | Haber et al. | 222/538 |
| 4,282,992 | 8/1981 | Chessler | 222/538 |
| 4,509,515 | 4/1985 | Altounyan et al. | 128/200.23 |
| 4,637,528 | 1/1987 | Wachinski et al. | 128/200.23 |

Primary Examiner—Edgar S. Burr
Assistant Examiner—Aaron J. Lewis
Attorney, Agent, or Firm—Wenderoth, Lind & Ponack

[57] ABSTRACT

An inhalator for use with aerosol containers of the type with an extendable and retractable mouthpiece comprises a tubular body intended to receive the aerosol container and having in its upper portion a cutout and a hinge pin for the delivery mouthpiece. The inhalator also includes a tubular cover rotatably applied to the tubular body and provided with a receptacle for receiving a delivery stem of the aerosol container and with a window for allowing extension of the mouthpiece, as well as with a mouthpiece actuating element so that, by rotating the cover until its window is in registry with the cutout in the tubular body, the mouthpiece will be brought to an extended position, and, by rotating the cover until its window is out of registry with the cutout in the tubular body, the mouthpiece will be brought to a retracted position. The delivery mouthpiece is provided on one side with a hinge which mates with the hinge pin which is fixed to the tubular body.

20 Claims, 3 Drawing Sheets

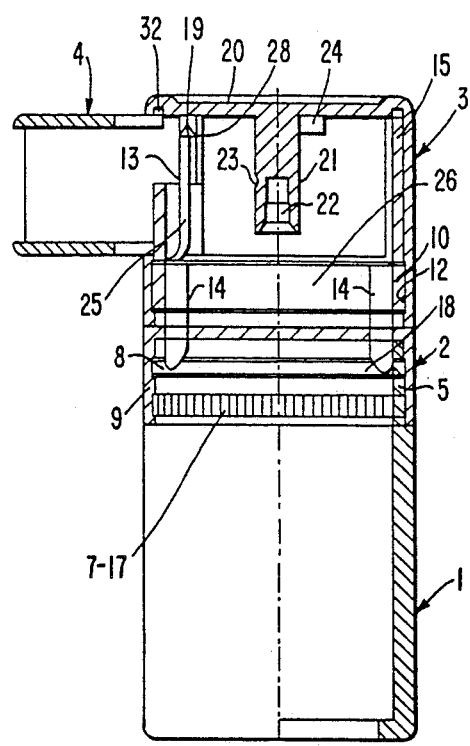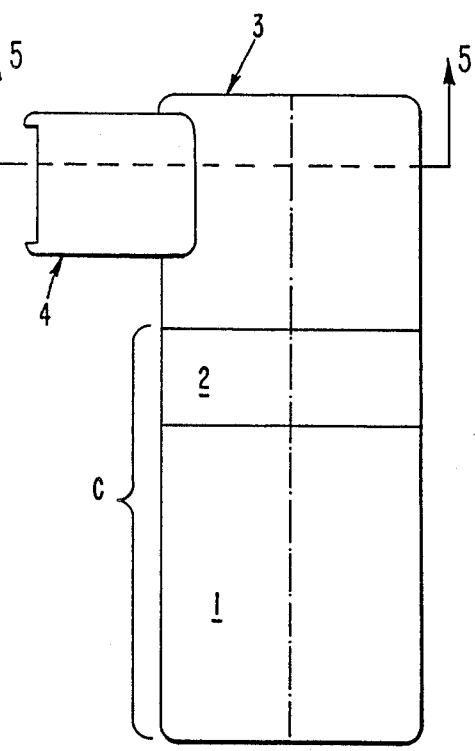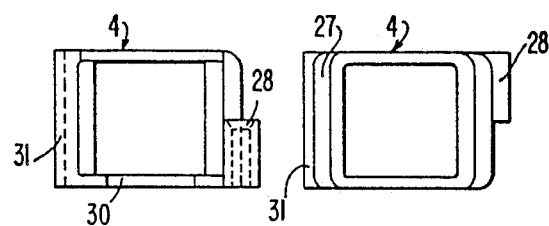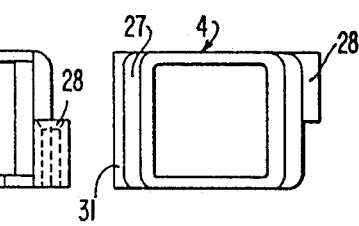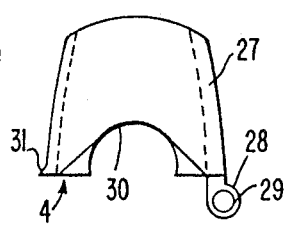

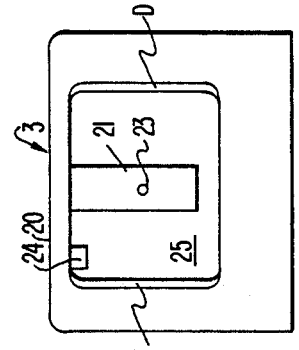
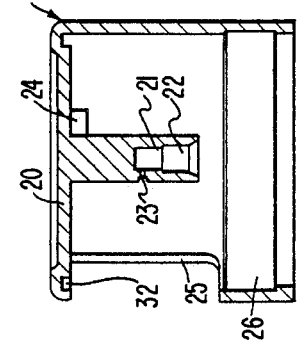
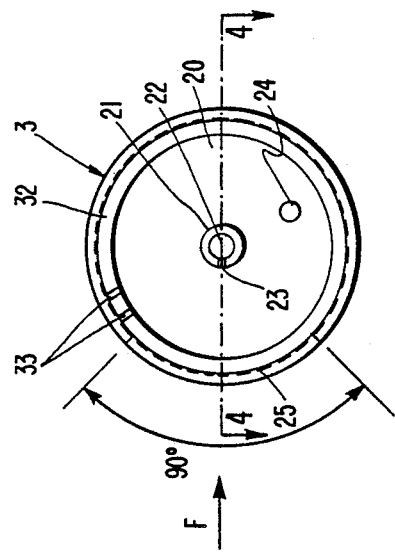
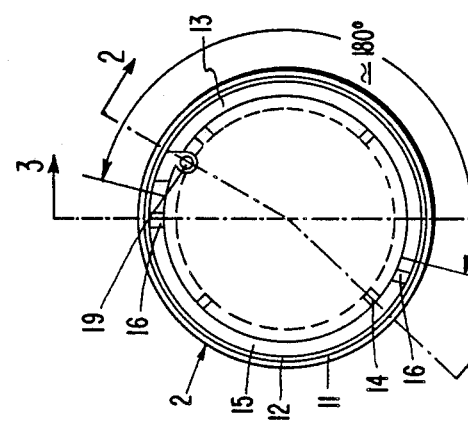
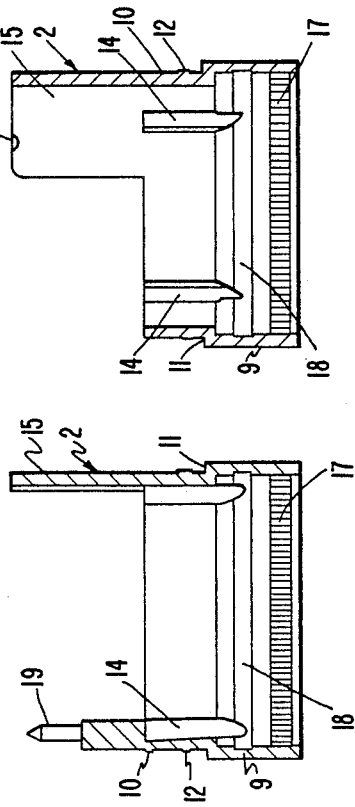

INHALATOR FOR AEROSOL CONTAINERS

BACKGROUND OF THE INVENTION

1. Field of the Invention

This invention generally relates to inhalators to be applied to aerosol containers containing medicaments or the like and, more particularly, to inhalators which are extremely simple and functional types both in their construction and from a hygienic standpoint.

2. Description of the Prior Art

As is known, aerosol containers for spraying medicaments or the like through an inhalator, the purpose of which is to convey the medicament in the form of spray directly into the mouth, the nose or the ear of a patient, have long been on the market.

Such known inhalators are usually of two types.

The first type consists of a cap with a fixed mouthpiece to be applied to an aerosol container in order that the spray from the valve of such aerosol container will flow through the mouthpiece directly into the oral, nasal or auricular cavity. Therefore, the purpose of such mouthpiece is to convey the spray of medicament directly into the area to be treated, thereby avoiding dispersion of sprayed medicament and contamination from the outside environment.

The second type consists of a cap with a mouthpiece which can be retracted into an inhalator body when the inhalator is not being operated and extracted therefrom whenever it is desired to spray the medicament. This type of inhalator was designed to protect the delivery orifice of an aerosol container valve against penetration of foreign matter into the mouthpiece and the inhalator itself, mainly for hygienic reasons.

In fact, the cleaning of the inhalator must be carried out according to stringent hygienic standards, which must be strictly followed. In the case of medicaments, the presence of any foreign matter has a deleterious effect on efficiency of the curative treatment.

The known inhalators of the second type, although on one hand offering several advantages over those of the first type, i.e. those having fixed mouthpieces on the other hand, suffer from several drawbacks. These drawbacks are mainly due to the rather complicated design which is required for the mouthpiece to accomplish its extraction and retraction movements. In addition, such inhalators have large openings to allow the mouthpiece to be extracted and retracted. Therefore, such inhalators fail in hygienically safeguarding the spraying mouthpiece and the sprayed medicament.

SUMMARY OF THE INVENTION

The purpose of this invention is to overcome the above shortcomings of inhalators having retractable and extractable mouthpieces, by providing an inhalator to be used with an aerosol medicament container or the like which ensures superior hygienic characteristics, has an extremely simple construction and provides for easy handling.

According to this invention, the inhalaor to be used with an aerosol container is of the type with a retractable and an extractable or extendable mouthpiece and comprises:

a tubular body intended to receive the aerosol container and having in its upper portion a cutout and a hinging means for the delivery mouthpiece;

a tubular cover rotatably applied to the tubular body and provided with a receptacle for the delivery stem of the aerosol container and with a window for allowing extension of the mouthpiece, as well as with a mouthpiece actuating element so that, by rotating the cover until its window is in registry with the cutout in the tubular body, the mouthpiece will be brought to an extended position, and, by rotating the cover until its window is out of registry with the cutout in the tubular body, the mouthpiece will be brought to a retracted position;

the delivery mouthpiece being provided on one side with a hinging means mating with a hinging means of the tubular body.

According to a feature of the present invention, the cutout in the tubular body covers roughly half of the wall of the tubular body and the hinging means of the tubular body consists of a pin located at an end of the cutout in the tubular body.

According to another feature of the present invention, the receptacle in the tubular cover has a spraying nozzle and the window of such cover is located in front of said nozzle.

According to a further feature of the present invention, the mating hinging means of the delivery mouthpiece essentially consists of an eyepiece for receiving the hinging pin of the tubular body.

According to a still further feature of the present invention, the tubular body is made of two tubular members intended to be fixed to each other so as to form a single piece.

BRIEF DESCRIPTION OF THE DRAWINGS

FIG. 1 is an axial section view of an inhalator according to the invention with its mouthpiece in an extended position;

FIG. 1A is a side elevational view of the inhalator of FIG. 1;

FIG. 2A is a plan view of the inhalator mouthpiece;

FIGS. 2B and 2C are a rear and front view, respectively, of the mouthpiece of FIG. 1;

FIG. 3A is a plan view of an upper body member of a two-piece tubular body of the inhalator of FIG. 1;

FIG. 3B is a sectional view of the upper body member, taken along line 2—2 of FIG. 3A;

FIG. 3C is a sectional view of the upper body member, taken along line 3—3 of FIG. 3A;

FIG. 4A is a bottom plan view of an inhalator cover;

FIG. 4B is a sectional view of the inhalator cover taken along line 4—4 of FIG. 4A;

FIG. 4C is a side elevational view of the inhalator cover as seen from the direction of arrow F in FIG. 4A;

DESCRIPTION OF THE PREFERRED EMBODIMENT

Figure 5A:
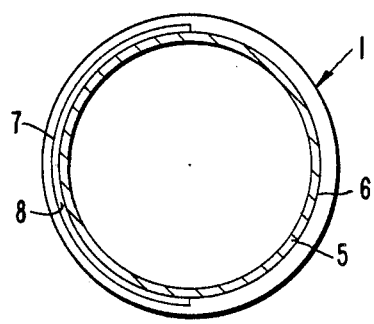
FIGS. 5A and 5B are a partially sectional top plan view and a partially sectional side elevational view, respectively, of a lower body member of the inhalator body.

Referring now to FIGS. 1 and 1A, the inhalator according to the invention comprises essentially a tubular body C, a tubular inhalator cover 3 and a mouthpiece 4. The tubular body C having a central longitudinal axis 100 consists of two members, namely a lower body member 1 and an upper body member 2.

Figure 5B:
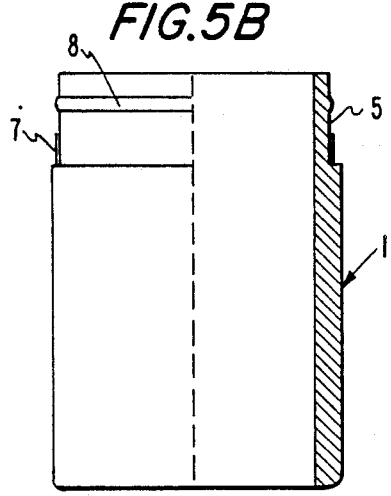

As shown in FIGS. 5A and 5B, the lower body member 1 has an upper portion 5 of slightly reduced diameter so as to form a step 6. Such upper portion 5 of reduced diameter has, just above step 6, an external circumferential knurl 7 and, above this knurl, a slightly protruding circumferential rib 8.

FIGS. 3A, 3B and 3C show the upper body member 2 in a top plan view, a sectional view taken along line 2—2 of FIG. 3A, and a sectional view taken along line 3—3 of FIG. 3A, respectively. The upper body member 2 has a lower portion 9 having the same inside diameter as the outside diameter of the upper portion 5 of the lower body member 1 and an upper portion 10 having the same outside diameter as the inside diameter of the tubular cover 3 (see FIG. 1). Between the two portions 9 and 10, a step 11 is formed and, just above step 11, a protruding rib 12 is provided on the external surface of the upper portion 10. The upper portion 10 of the upper body member 2 has a cutout 13 extending from the top of the upper portion 10 to a level of the upper portion 10 above rib 12 as shown in FIG. 3C. Cutout 13 circumferentially extends for about 180°. On the inner surface of upper body member 2, four ribs 14 are provided in order to guide an aerosol container when it is inserted into the inhalator. Two notches 16 are provided near each end of the upper edge of an upper body member wall 15. The purpose of such notches will be explained later. Inside the lower portion 9 of the upper body member 2, an internal knurl 17 is provided for engaging the external knurl 7 of the lower body member 1, and a circumferential groove 18, provided in the inner surface of the lower portion 9 of the upper body member 2 is intended to receive the circumferential rib 8 of the lower body member 1. In the cutout 13, a vertical pin 19 is provided for hinging the inhalator mouthpiece 4 and defining an axis parallel to the central longitudinal axis 100 of the tubular body C.

FIGS. 4A, 4B and 4C show the tubular cover 3 in a bottom plan view, a sectional view taken along line 4—4 of FIG. 4A, and an elevation view as seen from the direction of arrow F in FIG. 4A, respectively. As can be seen, cover 3 which has a central longitudinal axis coincident with the central longitudinal axis 100 of the tubular body C has its top end closed by a wall 20 to thereby form a cup-shaped member. The wall 20 includes shank 21 depending from a center portion thereof with an axial hole 22 therethrough for receiving a delivery stem of the aerosol container. A nozzle 23 allows passage of medicament sprayed from the aerosol container. A post 24, the purpose of which will be described later, also depends from the top wall 20. In front of the nozzle 23, the cover 3 has a rectangular window 25 extending circumferentially for about 90° to provide an opening through which the mouthpiece 4 can be extended. In a lower area of the inner surface of cover 3, a circumferential groove 26 is provided for accommodating the circumferential rib 12 of the upper body member 2. The groove 26 is preferably wider in the longitudinal direction than the rib 12 so as to allow longitudinal movemement of the rib 12 within groove 26. The top wall 20 is internally provided with a peripheral groove 32 intended to receive the upper edge of the wall 15 of the upper body member 2. Two projections 33 are provided in the groove 32, at a location diametrically opposite the post 24 to cooperate with notches 16 on the upper edge of the wall 15 of the upper body member 2, to form two limit stops. Cover 3, once applied to the upper body member 2, can rotate relative to the tubular body C.

FIGS. 2A, 2B and 2C show the mouthpiece in a plan, a rear and a front view, respectively. As can be seen, the mouthpiece 4 has slightly rounded sides 27 and is provided with a projecting element 28 through which a hole 29 is provided for receiving the pin 19 of the upper body member 2. A recess 30 is provided in a center portion of the rear portion of the mouthpiece 4 to receive the shank 21 of the cover 3 when the mouthpiece is retracted, and a stop flange 31 is provided on the side of the mouthpiece opposite the hinge element 28 as a limit stop to resist extension of the mouthpiece.

FIG. 1 shows an axial sectional view of the inhalator in an assembled condition. As can be seen, the tubular body C is assembled by snapping the upper body member 2 onto the lower body member 1. This is achieved by pressing the lower portion 9 of the upper body member 2 onto the lower portion 5 of the lower body member 1 until the circumferential rib 8 of the lower body member 2 snaps into the circumferential groove 18 of the upper body member 2 and knurls 7 and 17 are engaged with each other. Next, the pin 19 of the upper body member 2 is inserted into the hole 29 of the projecting element 28 of the mouthpiece 4, so that the pin acts as a hinge between the upper body member and the mouthpiece. Then, the cover 3 is applied such that the external circumferential rib 12 of the upper portion 10 of the upper body member snaps into the internal circumferential groove 26 of the cover 3, to thereby rotatably mount the cover 3 to the upper body member 2 with the upper edge of wall 15 of upper body member 2 engaging in the groove 32 of the top wall 20. The inhalator is thus assembled. An aerosol container can then be inserted into the tubular body C, until the protruding delivery stem of the aerosol container is inserted into the hole 22 through the shank 21 of the cover 3. The aerosol container is thus fastened to the inhalator and is held by the ribs 14 of the upper body member 2 which acts as spacer elements. A downwardly directed force applied against the cover top wall 20 is transmitted to the stem of the aerosol container valve, which is thus caused to open such that the medicament can flow from the nozzle 23, through the cover window 25 and the mouthpiece 4, to the outside.

Figure 6C:
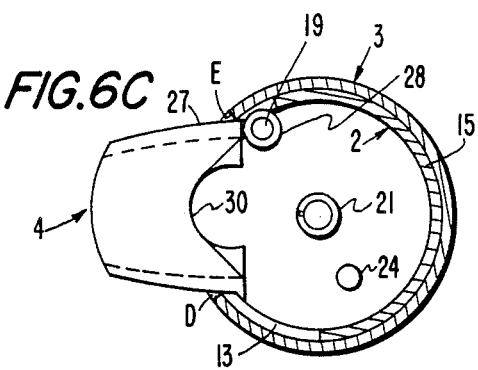
FIGS. 6A, 6B and 6C are sections taken along line 5—5 of FIG. 1A, showing the inhalator at various extension and retraction steps of the mouthpiece.
Figure 6B:
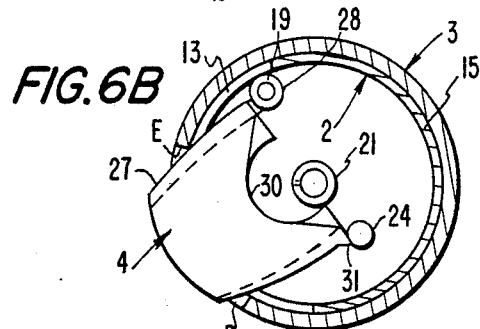
Figure 6A:
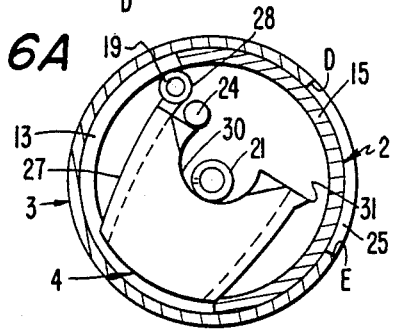

Extension and retraction movements of the mouthpiece 4 are illustrated in FIGS. 6A, 6B and 6C, which are sections taken along the line 5—5 of FIG. 1A, wherein the two basic components involved in the extension and retraction movements of the mouthpiece 4, namely the tubular body C and the cover 3, are shown.

As can be seen from these figures, the upper body member 2 is concentrically arranged inside the cover 3. These figures show the cover window 25 and the upper body member cutout 13 as well as the post 24, the shank 21 with the blind hole 22 and the nozzle 23, and the mouthpiece 4 hinged on the pin 19 by means of the hole 29 of the projecting hinge element 28.

FIG. 6A shows the inhalator in its closed condition, that is, with mouthpiece 4 retracted. In this condition, cover window 25 is in a position diametrically opposite the upper body member cutout 13, so that the inhalator will be tightly sealed. Also in this condition, the mouthpiece 4 is fully retracted and rests with its center recess 30 against the cover shank 21, post 24 is positioned near the hinge element 28 of the mouthpiece 4 and the front tip of the mouthpiece 4 is positioned in the cutout 13.

By rotating the cover 3 clockwise relative to the upper body member 2, the cover window 25 will be circumferentially shifted until it is positioned in front of the mouthpiece 4. In the meantime, post 24 will be rotated clockwise to a position where it contacts the portion of the mouthpiece 4 which is provided with the stop flange 31. By further rotating the cover clockwise relative to upper body member 2, the post 24 will cause the mouthpiece 4 to rotate clockwise until the front tip of the mouthpiece 4 is extended through the cover window 25 (see FIG. 6B).

By still further rotating cover 3 clockwise relative to the upper body member 2, an edge D of the cover window 25 contacts and causes the mouthpiece 4 to further rotate about pin 19. This rotation is continued until one of the ribs 33 in the groove 32 of the top wall 20 snaps into the relevant notch 16 in the upper body member wall 15, which thus acts as a limit stop to limit the opening movement of the inhalator (see FIG. 4A). When the inhalator is open (as shown in FIG. 6C), cover window 25 is in registry with the cutout 13 of the upper body member 2 and the mouthpiece 4 is at a fully extended position in front of the spray nozzle 23, with stop flange 31 resting against the edge D of the window 25.

To retract mouthpiece 4, it is sufficient to rotate the cover counterclockwise relative to the tubular body C.

When this rotation begins, an edge E of the cover window 25 contacts the mouthpiece side 27 facing the window 25, thus causing the mouthpiece to rotate counterclockwise about pin 19. This rotation of the window edge E is facilitated by the curvature of the mouthpiece side 27 on which the edge E slides. In the meantime, post 24 has rotated counterclockwise with the cover.

By further rotating the cover 3 counterclockwise relative to the body C, positions illustrated in FIG. 6B and FIG. 6A are successively reached. In the position shown in FIG. 6A, the mouthpiece 4 is fully retracted and resting with its center recess 30 against cover shank 21 and its tip in the cutout 13. In this position, the cover window 25 is closed by the wall 15 of the upper body member 2 and the cutout 13 is fully covered by the wall of the cover 3.

It is apparent from the foregoing that the inhalator according to the invention fully meets any hygienic requirements, because the spray of medicament never comes into contact with the environment since it is protected by the mouthpiece. The mouthpiece is, in turn, fully protected by the cover because, during the opening and closing operations of the inhalator, the space surrounding the mouthpiece never substantially contacts the external environment.

In addition, the inhalator according to the invention is of extremely simple design and easy to handle.

I claim:

1. An inhalator for use with an aerosol container having a delivery stem, comprising:
   a tubular body adapted to receive the aerosal container and having a cutout portion in an upper portion thereof and a central longitudinal axis;
   a cover having a window formed therethrough;
   means for mounting said cover to said tubular body for rotation about said central longitudinal axis between a first position in which said window and said cutout are misaligned and a second position in which said window and said cutout are in registry with one another;
   a mouthpiece; and
   means for mounting said mouthpiece to pivot about a pivot axis, parallel to said central longitudinal axis, between a retracted position in which said mouthpiece is disposed inside said cover and an extended position in which said mouthpiece extends outside said cover through said window and said cutout.

2. An inhalator as recited in claim 1, wherein said cover is cup-shaped.

3. An inhalator as recited in claim 1, wherein said cover has a receptacle means mounted thereto for receiving the delivery stem of the aerosol container.

4. An inhalator as recited in claim 1, wherein said receptacle means includes a nozzle means for allowing medicament to pass from the delivery stem of the aerosol container through said mouthpiece.

5. An inhalator as recited in claim 1, further comprising
   means for causing said mouthpiece to pivot between its retracted and extended positions when said cover is rotated between its first and second positions. respectively.

6. An inhalator as recited in claim 5, wherein said means for causing comprises a post depending from said cover and adapted to contact said mouthpiece upon rotation of said cover.

7. An inhalator as recited in claim 1, wherein said mouthpiece mounting means comprises a pivot pin mounted to said tubular member and a means, mounted to said mouthpiece, for rotatably receiving said pivot pin.

8. An inhalator as recited in claim 1, wherein said cover mounting means comprises a reduced diameter portion of said upper portion of said tubular body, and a lower portion of said cover member which has an inside diameter substantially equal to the outside diameter of said reduced diameter portion.

9. An inhalator as recited in claim 8, wherein said reduced diameter portion has a circumferential rib extending radially outwardly therefrom; and
   said lower portion of said cover member has a circumferential groove formed on an inside surface thereof adapted to receive said circumferential rib.

10. An inhalator as recited in claim 9, wherein said circumferential groove is significantly wider in a longitudinal direction than said circumferential rib such that said cover can be moved longitudinally relative to said tubular body.

11. An inhalator as recited in claim 1, wherein said tubular body comprises a lower body member having an upper portion and an upper body member having a lower portion mounted concentrically to said upper portion of said lower body member.

12. An inhalator for use with an aerosol container, comprising:
   a tubular body having a central longitudinal axis and an upper portion;
   a tubular cover member having a central longitudinal axis and being rotatably mounted to said tubular body, said central longitudinal axis of said tubular cover being coincident with said central longitudinal axis of said tubular body; and
   a mouthpiece hinged to said tubular body about an axis parallel to said longitudinal axes of said tubular body and said tubular cover.

13. An inhalator as recited in claim 12, wherein said tubular cover has a top wall closing a top end thereof.

14. An inhalator as recited in claim 13, further comprising
    a shank depending from a center portion of said top wall and having an axial bore therein adapted to receive a delivery stem of the aerosol container.

15. An inhalator as recited in claim 14, wherein
    said shank has a nozzle formed therethrough adapted to allow flow therethrough of medicament from the aerosol container.

16. An inhalator as recited in claim 13, further comprising
    a post depending from a portion of said top wall spaced from the center thereof and adapted to contact said mouth-piece upon rotation of said cover.

17. An inhalator as recited in claim 12, wherein
    said tubular body has a cutout portion in said upper portion thereof.

18. An inhalator as recited in claim 17, wherein
    said tubular cover has a window formed therethrough adapted to register with said cutout portion.

19. An inhalator as recited in claim 12, wherein
    said upper portion of said tubular body has a reduced diameter portion and said cover has a lower portion with an inside diameter substantially equal to the outside diameter of said reduced diameter upper portion of said tubular body.

20. An inhalator as recited in claim 19, wherein
    said reduced diameter portion has a circumferential rib extending radially outwardly therefrom; and
    said lower portion of said cover member has a circumferential groove formed on an inside surface thereof adapted to receive said circumferential rib.

* * * * *